US00PP29644P2

(12) United States Plant Patent
Egger

(10) Patent No.: US PP29,644 P2
(45) Date of Patent: Sep. 4, 2018

(54) ***HEUCHERA* PLANT NAMED 'TNHEUFR'**

(50) Latin Name: ***Heuchera* hybrid**
Varietal Denomination: TNHEUFR

(71) Applicant: Terra Nova Nurseries, Inc., Canby, OR (US)

(72) Inventor: Janet N. Egger, Wilsonville, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 15/731,557

(22) Filed: Jun. 27, 2017

(51) Int. Cl.
*A01H 5/02* (2018.01)

(52) U.S. Cl.
USPC ..... Plt./440

(58) Field of Classification Search
USPC ..... Plt./440
See application file for complete search history.

*Primary Examiner* — Susan McCormick Ewoldt
(74) *Attorney, Agent, or Firm* — Klarquist Sparkman, LLP

(57) ABSTRACT

A new and distinct *Heuchera* plant characterized by glossy, red to burgundy colored leaves, medium size, lobed and lightly ruffled leaves, small pink flowers in short spikes in August, good sun tolerance, a medium, low mounding habit with excellent crown count, and excellent vigor.

1 Drawing Sheet

Botanical denomination: *Heuchera* hybrid.
Variety designation: 'TNHEUFR'.

BACKGROUND OF THE INVENTION

The present invention relates to a new and distinct cultivar of *Heuchera* and given the cultivar name of 'TNHEUFR'. *Heuchera* is in the family Saxifragaceae. *Heuchera* 'TNHEUFR' originated as a controlled cross using *Heuchera* 'B265-2', a proprietary, unpatented, unnamed plant as the seed parent, and *Heuchera* 'K468-3', a proprietary plant as the pollen parent. These parents are a result of breeding plan to produce hardy red leaf *Heuchera* with good crowns.

Compared to the seed parent, *Heuchera* 'B265-2', the new cultivar has larger, redder leaves.

Compared to the pollen parent, *Heuchera* 'K468-3', the new cultivar has smaller leaves and more crowns.

Compared to *Heuchera* 'Fire Alarm', U.S. Plant Pat. No. 24,525, the new cultivar has smaller leaves, more crowns, and the leaves are redder and more ruffled.

Compared to *Heuchera* 'Fire Chief', U.S. Plant Pat. No. 21,880, the new cultivar has more crowns, the leaves are redder and more ruffled, and it is less free flowering.

Compared to *Heuchera* 'Mahogany', U.S. Plant Pat. No. 19,072, the new cultivar has red to burgundy leaves rather than red orange to red brown leaves.

This new *Heuchera* is uniquely distinguished by:

1. glossy, red to burgundy colored leaves,
2. medium size, lobed and lightly ruffled leaves,
3. small pink flowers in short spikes in August,
4. good sun tolerance,
5. a medium, low mounding habit with excellent crown count, and
6. excellent vigor.

This new cultivar has been reproduced only by asexual propagation (tip cuttings and tissue culture using growing tips). Each of the progeny exhibits identical characteristics to the original plant. Asexual propagation in 2013 by cuttings and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may change with variations in environment without a change in the genotype of the plant.

BRIEF DESCRIPTION OF THE DRAWINGS

FIG. 1 shows a one-year-old plant of *Heuchera* 'TNHEUFR' growing in shade in the trial bed in late August in Canby, Oreg.

FIG. 2 shows nine-month-old plants growing in the trial bed in full sun in October in Canby, Oreg.

DETAILED PLANT DESCRIPTION

The following is a detailed description of the new *Heuchera* cultivar based on observations taken in August of eight-month-old specimens growing in the trial field in August in Canby, Oreg. Canby is Zone 8 on the USDA Hardiness map. Temperatures range from a high of 95° F. in August to an average of 32° F. in January. Normal rainfall in Canby is 42.8 inches per year. The color descriptions are all based on The *Royal Horticultural Society Colour Chart,* 5$^{th}$ edition, 2007.

Plant:

*Form.*—Basal rosette, herbaceous perennial.
*Hardiness.*—USDA Zone 4 to 9.
*Size.*—16 cm tall from top of the foliage to the ground and 31 cm wide.
*Number of crowns.*—About 14.
*Habit.*—Medium, low mound.
*Vigor.*—Excellent.

Leaf:

*Type.*—Simple.
*Arrangement.*—Rosette.
*Shape.*—Widely depressed ovate.
*Number.*—About 70.
*Blade size.*—Grows to 10 cm long and 11 cm wide.

*Venation*.—Palmate.
*Lobing/division*.—Palmately lobed with 5 main lobes with secondary lobes.
*Margins*.—Crenate and undulate.
*Apex*.—Mucronulate.
*Base*.—Cordate, strongly overlapping.
*Surface texture*.—Glandular-puberulent on both sides.
*Leaf rugosity*.—Absent.
*Petiole description*.—Grows to 10.5 cm long and 3 mm wide, glandular hairs, Greyed Purple 187B.
*Leaf color*.—Spring and fall leaves, topside Greyed Purple 185A, bottom side 187C, summer new leaves, top side Greyed Purple 187C including veins, bottom side Greyed Purple 187B, including veins; summer mature leaves topside Greyed Purple 187A, bottom side Greyed Purple 187B; winter leaves top side Greyed Red 178A, bottom side Greyed Purple 187C.

Inflorescence:
*Size*.—Grows to 5 cm wide and 13 cm long.
*Type*.—Upright thyrse.
*Number of flowers per thyrse*.—About 80.
*Flower density*.—Moderate to light.
*Number of thyrse*.—About 10.
*Peduncle*.—Grows to 26 cm long and 3 mm wide at base, glandular hairs, Greyed Purple 187B.
*Pedicel*.—Grows to 3 mm long, with glandular hairs, Greyed Purple 187B.
*Bloom period*.—August in Canby, Oreg.

Flower bud:
*Size*.—3 mm wide and 4 mm long.
*Description*.—Glandular puberulent, ovoid, down facing.
*Color*.—Red Purple 64A.

Flower:
*Type*.—Perfect.
*Shape*.—Campanulate.
*Attitude*.—Side-facing.
*Size*.—5 mm long and 3 mm wide.
*Corolla description*.—5 petals, each 2.5 mm long and 1 mm wide, spatulate, margins entire with 0 to 5 lobes, tip acute, glabrous on topside, glandular-puberulent on bottom side, both sides White NN155C.
*Calyx description*.—Campanulate, 6 mm long and 4 mm wide, with 5 lobes with wide sinuses divided ½ way to the base, each 2 mm wide and 3 mm long, oblong in shape, back side glandular-puberulent with glandular hairs, glabrous inside, tip obtuse, margin entire, outside Red Purple 63C blending to Red Purple 64A at the base, inside Red Purple 63C.
*Stamen description*.—5 in number, filaments 2.5 mm long, White NN155C, anthers 0.5 mm long, Yellow Orange 22A, pollen slight Yellow Orange 22A.
*Pistil description*.—1, 2-beaked, 6 mm long and 2 mm wide, Red Purple 62D overall, ovary 2 mm long and 2 mm wide, style 4 mm long.
*Fragrance*.—None.
*Lastingness*.—Each thyrse blooms for about 3 weeks on the plant.

Fruit:
*Type*.—Two-beaked ovoid capsule.
*Fertility*.—Low.
*Color*.—Greyed Brown 199C.

Seed:
*Shape*.—Linear.
*Size*.—2 mm long.
*Color*.—Black 202A.

Pest and disease tolerance: The new cultivar is typical to the genus. No known resistances to pests or diseases. No problems have been found in Canby, Oreg.

I claim:

1. A new and distinct *Heuchera* plant as herein illustrated and described.

* * * * *

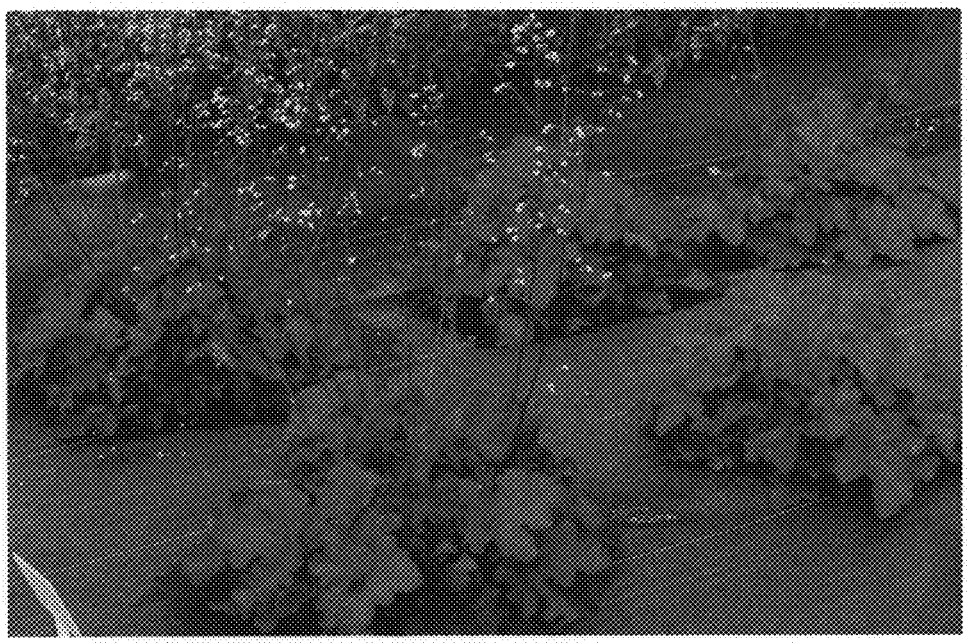

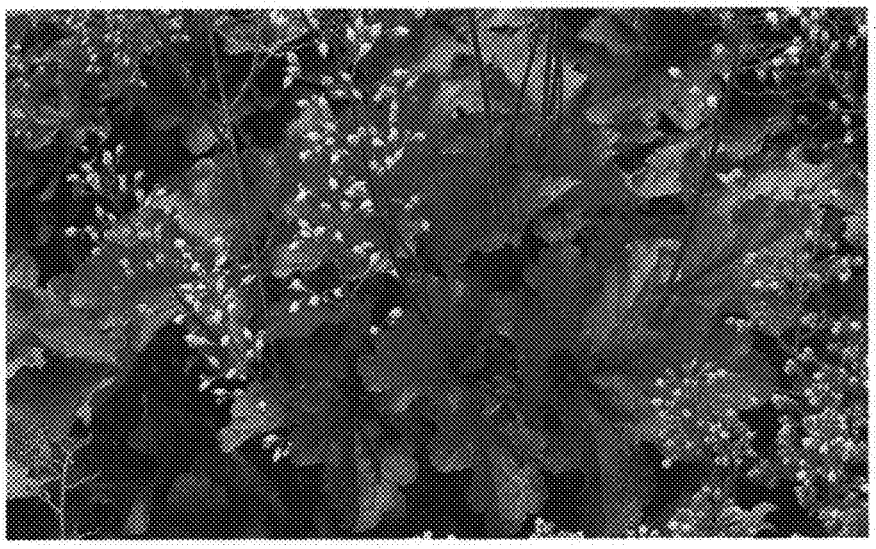
FIG 1. above
FIG 2 below